United States Patent
Hasselberg et al.

(10) Patent No.: US 11,904,179 B2
(45) Date of Patent: Feb. 20, 2024

(54) VIRTUAL REALITY HEADSET AND SYSTEM FOR DELIVERING AN INDIVIDUALIZED THERAPY SESSION

(71) Applicant: UNIVERSITY OF ROCHESTER, Rochester, NY (US)

(72) Inventors: Michael J. Hasselberg, Rochester, NY (US); David John Mitten, Rochester, NY (US); Kostantinos Vasalos, Rochester, NY (US); Wendy Cross, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 192 days.

(21) Appl. No.: 17/487,863

(22) Filed: Sep. 28, 2021

(65) Prior Publication Data
US 2022/0096863 A1 Mar. 31, 2022

Related U.S. Application Data

(60) Provisional application No. 63/085,269, filed on Sep. 30, 2020.

(51) Int. Cl.
*A61N 5/06* (2006.01)
*G06F 3/01* (2006.01)
*G09B 19/00* (2006.01)
*G06F 3/16* (2006.01)

(52) U.S. Cl.
CPC .......... *A61N 5/0618* (2013.01); *G06F 3/012* (2013.01); *G06F 3/165* (2013.01); *G09B 19/00* (2013.01); *A61N 2005/0626* (2013.01); *A61N 2005/0648* (2013.01)

(58) Field of Classification Search
CPC .......... A61N 5/0618; A61N 2005/0626; A61N 2005/0648; G06F 3/012; G06F 3/165; G09B 19/00
See application file for complete search history.

(56) References Cited

U.S. PATENT DOCUMENTS

| 9,449,150 B2 * | 9/2016 | Hyde | G16H 20/10 |
| 2018/0338727 A1 * | 11/2018 | Mukhopadhyay | A61B 5/721 |
| 2020/0178885 A1 * | 6/2020 | Orr | A61B 5/486 |

* cited by examiner

*Primary Examiner* — Timothy A Musselman
(74) *Attorney, Agent, or Firm* — Kilpatrick Townsend & Stockton LLP

(57) ABSTRACT

An individualized therapy session can be delivered to a patient using a virtual reality headset and system. In one example, the system can include an accelerometer and a processor. The processor can receive data detected by the accelerometer. The data can include head position data and head movement data. The processor can then determine a view direction of a user of the VR device using the head position data, determine a heart rate of the user by using the view direction of the user to process the head movement data, and output the heart rate of the user to a remote device. The processor can receive, from the remote device, a command to adjust a VR session presented by the VR device to the user. Based on the command, the processor can adjust one or more parameters of the VR session presented by the VR device.

20 Claims, 6 Drawing Sheets

VIRTUAL REALITY HEADSET AND SYSTEM FOR DELIVERING AN INDIVIDUALIZED THERAPY SESSION

CROSS-REFERENCE TO RELATED APPLICATION

This claims the benefit of priority under 35 U.S.C. § 119(e) to U.S. Provisional Patent Application No. 63/085,269, filed Sep. 30, 2020, the entirety of which is hereby incorporated by reference herein.

TECHNICAL FIELD

The present disclosure relates generally to virtual reality devices. More specifically, but not by way of limitation, this disclosure relates to a virtual reality headset and system for delivering individualized therapy sessions to patients.

BACKGROUND

In some areas of the world, behavioral health conditions are the third most frequently diagnosed condition in hospital emergency departments. Additionally, those admitted into the hospital are 22% more likely to be readmitted than those without comorbid mental illness. Despite the growing evidence that psychiatric care is valuable, few adults with behavioral health conditions get treatment due to lack of access.

Cognitive behavioral therapy (CBT) is one type of psychological treatment for biobehavioral responses to anxiety and stress. CBT can be a time-limited psychotherapeutic approach that focuses on the relationships among cognitions, emotions, and behaviors, and encourages patients to adopt an active problem-solving approach to cope with distress. This treatment approach can improve functioning and quality of life for patients with anxiety symptomology. But a lack of trained therapists, stigma, cost, and geographic barriers can result in many patients remaining untreated.

SUMMARY

One example of the present disclosure includes a virtual reality (VR) device comprising an accelerometer, a processor, and a memory including instructions that are executable by the processor for causing the processor to perform operations. The operations can include receiving data detected by the accelerometer, the data including head position data and head movement data; determining a view direction of a user of the VR device using the head position data; and determining a heart rate of the user by using the view direction of the user to process the head movement data. The operations can also include outputting the heart rate of the user to a remote device; receiving, from the remote device, a command to adjust a VR session presented by the VR device to the user; and adjusting, based on the command, one or more parameters of the VR session presented by the VR device.

Another example of the present disclosure includes a method involving receiving data detected by an accelerometer of a virtual reality (VR) device, the data including head position data and head movement data; determining a view direction of a user of the VR device using the head position data; and determining a heart rate of the user by using the view direction of the user to process the head movement data. The method also involves outputting the heart rate of the user to a remote device; receiving, from the remote device, a command to adjust a VR session presented by the VR device to the user; and adjusting, based on the command, one or more parameters of the VR session presented by the VR device. Some or all of the method steps can be implemented by a processor.

Still another example of the present disclosure includes a non-transitory computer-readable medium comprising program code that is executable by a processor for causing the processor to perform operations. The operations can include receiving a heart rate determined by a virtual reality (VR) device from data detected by an accelerometer of the VR device, the data including head position data and head movement data, and the heart rate being of a user wearing the VR device during a VR therapy session. The operations can include comparing the heart rate to a threshold heart rate. The operations can include, in response to comparing the heart rate to the threshold heart rate, determining a modification to the VR therapy session. The operations can include generating a command for controlling one or more parameters of the VR therapy session presented by the VR device in accordance with the modification. And the operations can include transmitting the command to the VR device.

This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

The foregoing, together with other features and examples, will become more apparent upon referring to the following specification, claims, and accompanying drawings.

DETAILED DESCRIPTION

Figure 1:
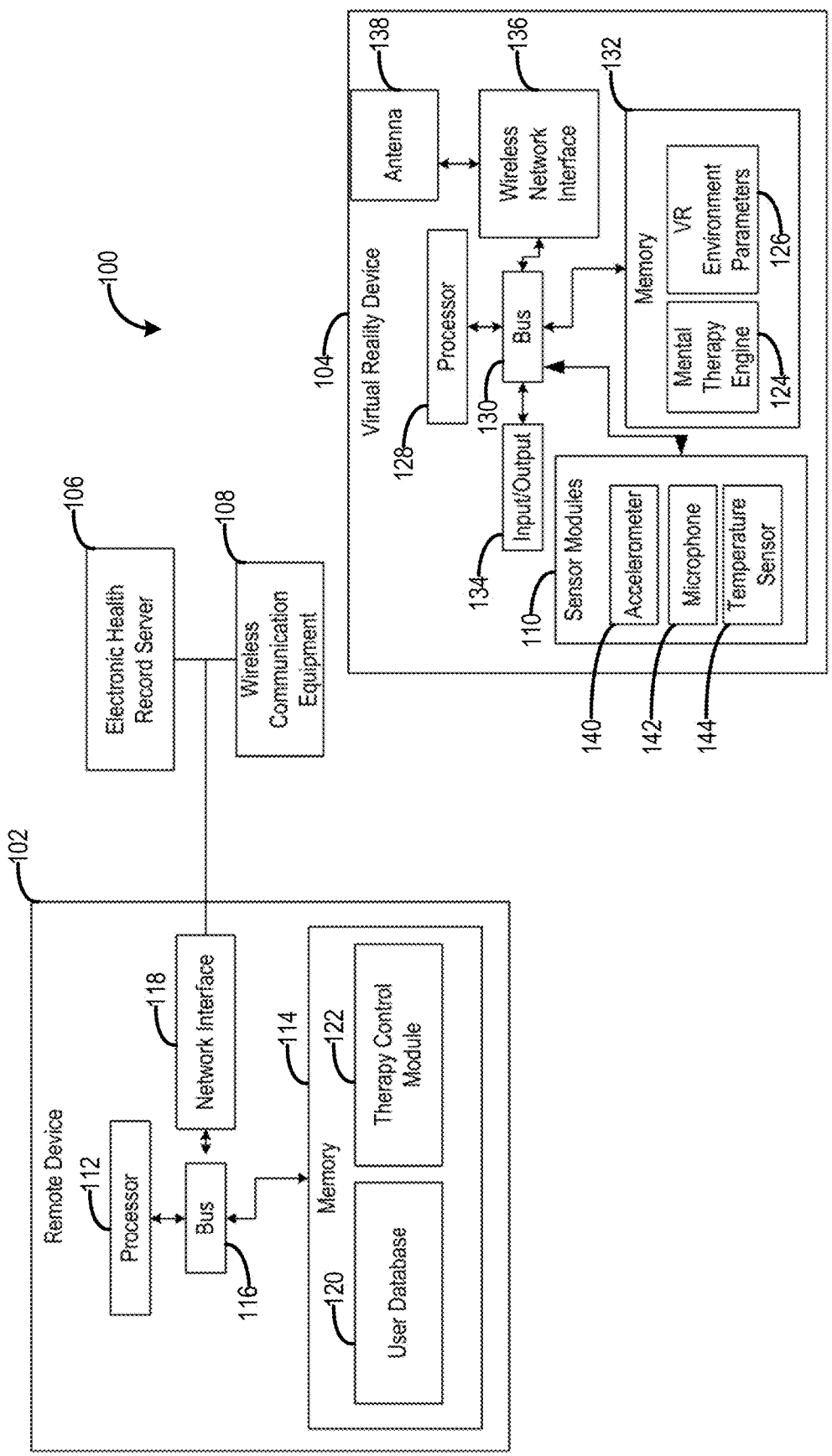
FIG. 1 is a block diagram of an example of a computing environment for delivering an individualized medical health treatment according to some aspects of the present disclosure.

Certain aspects and features relate to delivering individualized mental health therapies by using a virtual reality (VR) device that can detect information about a patient during an immersive mental therapy treatment and customize the mental health therapy. An example of a mental health therapy is cognitive behavioral therapy (CBT) by which a VR device can deliver an immersive environment for presenting treatment modules to a patient. The VR device can detect patient physiological characteristics (e.g., heart rate, respiration rate, and other vital information) that can be used by the system to modify virtual reality content that is delivered to the patient. For example, the VR device can include an accelerometer and a processor that can use detected head position data and head movement data to determine the direction that user of the VR device is viewing. The view direction of the user can be used to process the head movement data to determine the heart rate of the user. The heart rate of the user can be used, potentially along with other data, to modify the therapy session being delivered using the VR device.

In one example, a system can be implemented via a VR device and a suite of sensors to provide an evidence-based behavioral health therapy that can use the skill of remotely located clinicians rather than requiring the clinicians to be located with each patient or user. The system can be focused on the management of anxiety and stress and the efficacy increased by using real-time patient physiological responses to modify the therapy.

Despite the growing evidence that psychiatric care is valuable, few adults with behavioral health conditions get treatment due to lack of access. A lack of trained therapists, stigma, cost, and geographic barriers can result in many patients remaining untreated. By using one or more examples of the present disclosure, access to behavioral health care can be increased and the quality of care may be improved. In particular, delivering a medical treatment through virtual reality systems can ameliorate these barriers by leveraging technology to extend behavioral health service delivery outside of traditional clinic walls.

To be effective and to maximize the positive response of the patient to the treatment protocol, the system can include a suite of sensors including sensors such as an accelerometer, a microphone, or a gaze tracking sensor. By tracking the physiological responses of a patient during a treatment protocol, a remote device (e.g., a computing device accessible by a licensed provider) can receive physiological measurements from the VR device. The healthcare provider can control the VR environment based on the behavioral response indicated by the physiological measurements. A system according to various examples can allow for automated provider adjustment of the treatment protocol during a treatment and can guide care pathways used to intervene when certain patient behaviors are indicated by the physiological measurements (e.g., excessive heart rate, hyperventilation, etc.).

In one example, a system includes a software application that can execute on a VR device, such as a wearable headset with computing functionality, and includes a server subsystem that can dynamically control the application and provide content for delivery by the application to the user. The server subsystem can also link to a remote device accessible by a provider for controlling the VR treatment protocol. The server subsystem can also link to an electronic health record (EHR) subsystem to leverage the data security, data relationships, and provider information in the EHR subsystem. The software application can include any number of immersive environments arranged in a sequence of modules to elicit physiological responses from the patient that can be measured. Examples of the immersive environments can include: psychotherapy, animated videos, and images based on the principles of CBT, supplementary material, and skills practice homework assignments. During each module, the sensors can monitor a patient's physiological responses such as heart rate, respiratory rate, blood pressure, skin temperature, and the like. The physiological measurements from the sensors can be used by a clinician or other service provider accessing the system to control one or more VR environment parameters such as audio intensity, type of environment, light intensity, and the like. The physiological measurements from the system can be used identify the type of patients that may need a higher (or lower) level of care and to identify patients that may be at increased risk for poor outcomes. Tracking patient physiological responses during a treatment can result in effective coordination and triage of patients to the appropriate level of care based on a patient's physical response to a VR environment.

These illustrative examples are given to introduce the reader to the general subject matter discussed here and are not intended to limit the scope of the disclosed concepts. The following sections describe various additional features and examples with reference to the drawings in which similar numerals indicate similar elements but, like the illustrative examples, should not be used to limit the present disclosure.

FIG. 1 is a block diagram of an example of a computing environment 100 for delivering an individualized medical health treatment according to some aspects of the present disclosure. The computing environment 100 includes a remote device 102. The remote device 102 may be operable by a healthcare provider. The computing environment 100 also includes a VR device 104. The VR device 104 may be operable by a patient. The computing environment 100 further includes an electronic health record server 106 and various wireless communication equipment 108.

The remote device 102 may be any suitable type of computing device for providing commands or parameters that adjust content (e.g., audio or visual content) being presented by the VR device 104. Examples of the remote device 102 can include a desktop computer, a laptop computer, a server, or a mobile phone. The remote device 102 may contain any suitable hardware, such as a processor 112 and memory storage 114. The processor 112 may be coupled to the memory storage 114 via a communication bus 116. The processor 112 may also be coupled to a network interface 118 for communicating with other components of the computing environment 100, for example, the VR device 104.

The remote device 102 may also connect with an electronic health record server 106 to access an electronic health record of a patient associated with the VR device 104. In one example, the electronic health record server 106 stores multiple electronic health records for various patients. For instance, the electronic health record server 106 may store a group of patients being treated for a set of health conditions, a group of patients being treated within a specific geographic region, or a group of patients being treated by a set of defined providers (e.g., a health system, a private practice, a group of private practices, etc.).

In some examples, the remote device 102 may include a user database 120 (such as a patient or provider database) and a therapy control module 122. In one example, the user database 120 may store detailed profile information regarding various medical therapy providers, patients, or both of these. Examples of the profile information for a medical therapy provider can include a name, license number, and practice information. Examples of profile information for a patient can include a name, medical status, current provider, prescribed therapy, patient risk classification, etc. The therapy control module 122 may provide the VR device 104 with parameters or commands for controlling one or more VR environment parameters 126 that are used to present the VR treatment to the patient. Examples of VR environment parameters 126 may include a customizable environment location, an ambient sounds profile, or other environmental aspects that may be presented by the VR device 104 as described in some aspects of the present disclosure.

The VR device 104 may be any suitable computing device for presenting a therapy module to a user in a VR environment. Examples of the VR device 104 may include a desktop computer, a laptop computer, a wearable computing device (e.g., a headset or glasses), or a mobile phone. The VR device 104 may include any suitable hardware, such as a processor 128 communicatively coupled by a communication bus 130 to a memory storage 132, various input/output connectors 134, a wireless network interface 136, and an antenna 138. In some examples, the VR device 104 may present a VR environment to the user based on VR environment parameters 126, which may be adjusted by the remote device 102. The VR device 104 may present the therapy module in a mental therapy engine 124 to a user using audio, video, or location cues. For instance, the VR device 104 may present a video of a therapy module. The video may be a 360-degree video or VR environment. In some examples, the VR device 104 may collect patient physiological measurements using sensor modules 110 that can be internal or external to the VR device 104. The VR device 104 can send the physiological measurements or corresponding metrics to the remote device 102.

In some cases, the VR device 104 may interact with the remote device 102 via an application programming interface, a cloud-based application, or a standalone application that is downloaded to the VR device 104 from any suitable source, such as the remote device 102. The VR device 104 may output the physiological measurements or metrics associated with the user to the remote device 102 via various networking interfaces, direct communication protocols, or existing medical protocols.

The remote device 102 and the VR device 104 may communicate with one another via one or more communication networks, such as a local area network or the Internet. The remote device 102 and the VR device 104 may communicate using one or more wired or wireless internet connections. The remote device 102 and the VR device 104 may also communicate with the electronic health record server 106 via the one or more communication networks. In some examples, the remote device 102 and the VR device 104 may communicate with the electronic health record server 106 via an internet portal or application programming interface.

Although FIG. 1 shows a certain number and arrangement of components, this is for illustrative purposes and intended to be non-limiting. Other examples may include more components, fewer components, different components, or a different arrangement of the components than is shown in FIG. 1. For instance, the sensor modules 110 may be external and communicatively coupled to the VR device 104 in other examples.

Figure 2:
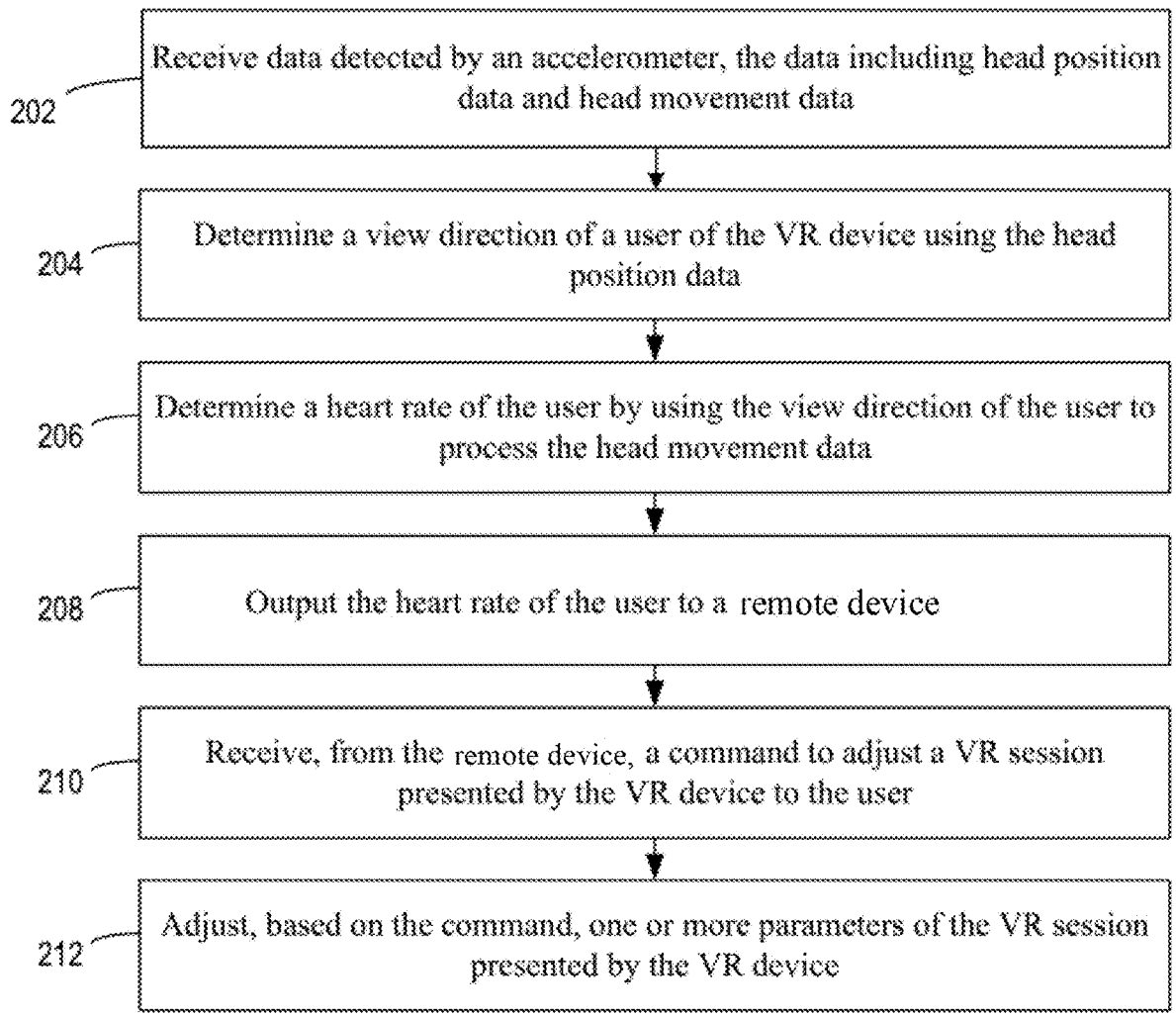
FIG. 2 depicts a flowchart of an example of a process for controlling one or more parameters of a virtual reality treatment according to some aspects of the present disclosure.

FIG. 2 depicts a flowchart of an example of a process 200 for controlling one or more parameters of a VR treatment according to some aspects of the present disclosure. Other examples may include more operations, fewer operations, different operations, or a different order of the operations shown in FIG. 2. In some examples, the VR device 104 described above can execute the some or all of process 200.

At block 202, the process 200 involves receiving data detected by an accelerometer 140 in the sensor modules 110 described above with regard to FIG. 1. The accelerometer 140 can be used to detect head position data (e.g., head position and orientation) and head movement data by measuring accelerations caused by a changing position or orientation of the VR device. For example, the VR device 104 can detect a head position based on an initial position of the VR device 104 when the sensor modules 110 detect that the VR device 104 has been placed on a user's head. For instance, the VR device 104 can use an altimeter, an acoustic measurement of position, or GPS to determine an initial position. The VR device 104 may compute a displacement from the initial position by detecting changes in the measurements of various sensor modules 110 included in the VR device 104 or otherwise communicatively coupled to the VR device 104. The VR device 104 can use measurements of the accelerometer 140 to determine a position by dead-reckoning a new position or to determine a new position from a measurement of the GPS. The data measured by the accelerometer 140 may be received by a processor 128 of the VR device 104.

At block 204, the process 200 involves determining a view direction of a user of the VR device 104 using head position. For instance, the VR device 104 can have a reference frame when placed on the head of a user. The VR device 104 can determine, based on the reference frame, a view direction that corresponds to the face of a user. The view direction may be a three-dimensional direction with the head position defined in a three-axis coordinate system. For example, the VR device 104 can detect a gravity vector; a lateral axis that may correspond to an axis that passes through a viewing area, the head of the user, and the accelerometer 140; and longitudinal axis that is perpendicular to the lateral axis. The VR device 104 may compute a reference frame based on one or more axis. The VR device 104 can assign a coordinate system, such as a Cartesian coordinate system (x, y, z), to the reference frame of the VR device 104 when placed on the head of the user. The VR device 104 can determine a deviation from an origin position in the coordinate system to compute the view direction of the user. The VR device 104 may use an origin vector that describes an initial position of the VR device 104 on the user's head and compute a displacement from the origin position. The VR device 104 may determine the view direction as aligned with a displaced position of the lateral axis.

At block 206, the process 200 involves determining a heart rate of the user by using the view direction of the user to process the head movement data. For instance, the accelerometer 140 can detect head movements that are associated with a heartbeat in the head of the user that is wearing the VR device 104. The head movements may correspond to movement of blood through the user's head or neck blood vessels and may therefore serve as a ballistic cardiogram. The view direction can then be used to determine and isolate the appropriate vector for analysis of the ballistic cardiogram. The accelerometer 140 can use noise filtering techniques such as a high pass filter to identify the heartbeat in the view direction. In one example, the heart rate can be determined by performing a fast Fourier transform (FFT) of the head movement data in the view direction. The VR device 104 may sample the accelerometer 140 at a rate that corresponds to the ballistic forces that are caused by functioning of the heart. While block 206 is described using heart rate, the VR device 104 may also determine other physiological measurements such as skin temperature, eye dilation, respiratory rate, and the like.

At block 208, the process 200 involves outputting the heart rate of the user to a remote device, such as the remote device 102 of FIG. 1. The VR device 104 may use a wireless network interface 136 and an antenna 138 to communicate to the remote device 102. The VR device 104 may encode or encrypt the heart rate of the user or other physiological measurements of the user prior to outputting the physiological measurements to the remote device 102. In some examples, physiological measurements may be stored on the VR device 104 for a period of time and output in a batch form. The VR device 104 may also use a tunneling or wrapping of the physiological measurements to prevent unauthorized access to medical information of the user.

The VR device 104 may also output identifying information of the user associated with the heart rate, and such information stored in a memory storage component of the VR device 104. The VR device 104 may send a portion of the identifying information (e.g., patient profile number, provider assignment information, social security number, username, etc.) to the remote device 102 for authentication purposes. The remote device 102 may identify a particular patient record from multiple patient records based on the identifying information. The remote device 102 may then associate the VR device 104 with the particular patient record and allow the provider to access stored data relating to the particular patient record.

At block 210, the process 200 involves receiving, from the remote device 102, a command to adjust a VR session presented by the VR device 104. The remote device 102 may transmit commands or control inputs to the VR device 104 based on the received heart rate or other physiological measurements of the user.

In some examples, the commands and control inputs may be atomically generated by the therapy control module (e.g., with little or no human interaction). For example, the remote device 102 can determine the commands and control inputs based on a lookup table. In some such examples, the remote device 102 may include a lookup table that maps certain physiological measurements or combinations of physiological measurements to certain therapy modules. The remote device 102 can select a therapy module using the lookup table based on the user's physiological measurements, generate one or more commands based on the selected therapy module, and transmit the one or more commands to the VR device 104. Alternatively, the lookup table can map certain physiological measurements or combinations of physiological measurements to certain commands. The remote device 102 can determine the command based on a correlation in the lookup table between the user's physiological measurements and the command. The remote device 102 can then transmit the command to the VR device 104.

In some examples, the remote device 102 can determine the commands and control inputs based on one or more algorithms. For example, the remote device 102 may include an algorithm in which one or more physiological measurements can be input as variable values to compute certain results. The remote device 102 can then select a command based on the results and transmit the command to the VR device 104. As one particular example, the algorithm can weight different physiological factors to generate a weighted score associated with the user. The weighted score can then be compared to a predefined threshold. If the weighted score exceeds the predefined threshold, a first command may be selected. If the weighted score is below the predefined threshold, a second command may be selected.

In some examples, the remote device 102 may be accessed by a healthcare provider who can operate the therapy control module 122 to adjust one or more VR environment parameters 126 being presented to the user. The therapy control module 122 may generate the commands for the VR device 104 and send one or more commands via the network interface 118 to the VR device 104. The VR device 104 may receive one or more commands from the remote device 102 and responsively update the VR environment parameters 126 or adjust the content being presented to the user.

For instance, a healthcare provider accessing the remote system 102 may determine that a heart rate of a user has increased or decreased, for example beyond a threshold limit, during the treatment session. Based on this change in heart rate, the provider may use the therapy control module 122 to make an adjustment to the VR device 104 content presented to the user. In some examples, the provider may determine that the heart rate change or other physiological measurements change of a particular user necessitates medical escalation. The therapy control module 122 may provide commands to the VR device 104 relating to such an escalation, for example by presenting a therapist call number, emergency department contact information, additional resources, or an indicator to seek urgent medical care. Additionally or alternatively, the provider may input adjustments to one or more VR environment parameters 126. The remote device 102 can generate commands to control the content that is presented to the user based on the adjusted VR environment parameters 126.

At block 212, the process 200 involves adjusting, based on the command, one or more parameters of the VR session presented by the VR device 104. For example, the therapy control module 122 may provide the VR device 104 with parameters or commands for controlling one or more VR environment parameters 126 that are used to present the VR treatment to the patient. Examples of parameters that may be adjusted may include a customizable environment location, an ambient sounds profile, or other environmental aspects (e.g., auditory or visual aspects) that may be presented by the VR device 104.

In some examples, the remote device 102 may also include a machine-learning component, such as a neural network or classifier. The machine-learning component can be trained on historical data. Once trained, the machine-learning component can analyze the heart rate or other physiological measurements of a user of the VR device 104. In some cases, the machine-learning component can be configured to predict expected physiological measurements, such as an elevated heart rate in response to a particular set of VR environment parameters 126, based on a set of inputs. The inputs may include current or past physiological measurements of the user, VR environment parameters 126, or any combination of these. The remote device 102 can use the predictions to preemptively control the VR treatment based on the expected physiological measurements. For example, the remote device 102 can determine one or more commands based on the expected physiological measurements. The remote device 102 can then transmit the one or more commands to the VR device 104. In some examples, the commands may be configured to alleviate or counter an escalating physiological response. This may help prevent medical problems before they arise, for example if the user of the VR device 104 is experiencing an escalating heart rate in response to the VR treatment.

Figure 3:
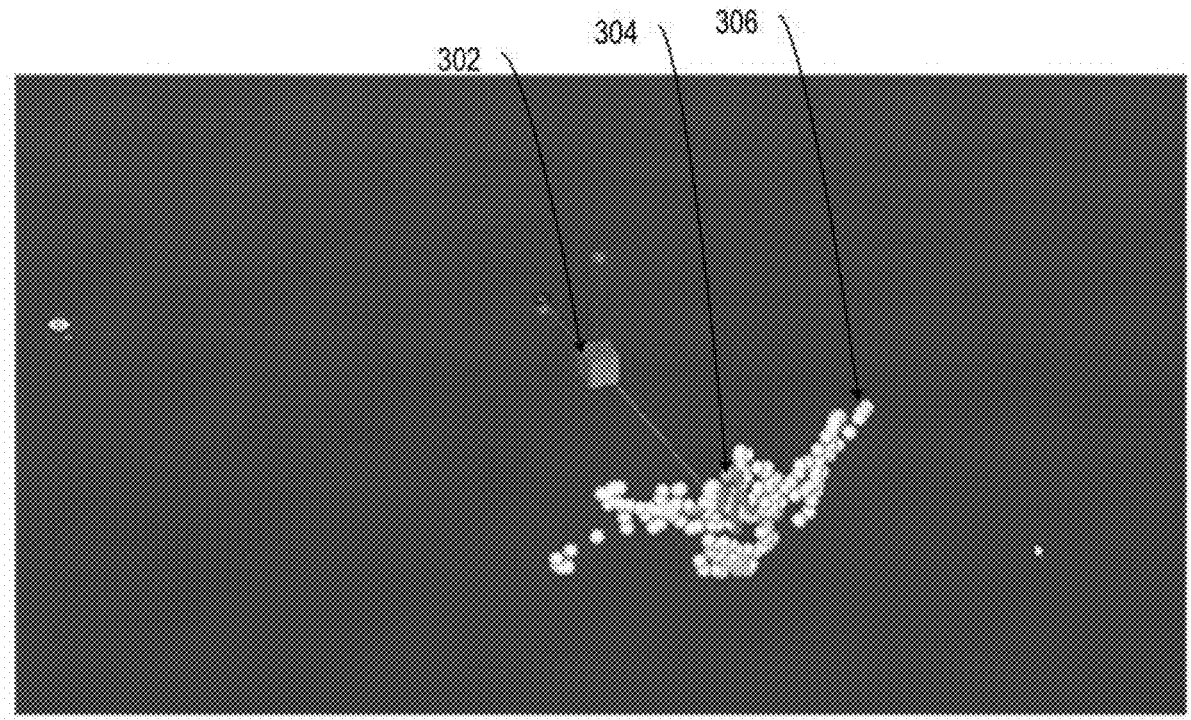
FIGS. 3-5 depict examples of measured head movements and viewing directions usable to determine the heart rate and other physiological measurements of a user according to some aspects of the disclosure.

As noted above, head movements and viewing directions can be used to determine the heart rate and other physiological measurements of a user according to some aspects of the disclosure. FIG. 3 depicts an example of a view direction, a head position 302, and a reference frame (e.g., the axis) that can be determined for measuring the head movement data according to aspects of the present disclosure. FIG. 3 also depicts a first measurement 304 at which the measured physiological responses indicate a first state of the user of the VR device 104 and a second measurement 306 at which the measured physiological responses indicate a second state of the user of the VR device 104. The VR device 104 can measure various forces acting on the head of the user and, from this data, determine physiological measurements. For example, the VR device 104 can determine a heart rate of the user by detecting a force generated by movement of blood through the user's head or neck blood vessels. The VR device 104 can detect ballistic forces caused by the blood moving within the blood vessels that can be used to derive a heart rate of the user. The VR device 104 can derive the heart rate by setting a sample rate of the accelerometer, or filtering a sample rate of the accelerometer, to a rate that corresponds to a heart rate of the user.

A state (e.g., a cognitive state) of the user can be determined based on the measurements by the sensors of the VR device 104. For instance, the VR device 104 may determine the heart rate of the user and determine that the user is in a meditative state at a first measurement time. The VR device 104 may also determine that the user is in a conscious, or non-meditative, state at a second measurement time. The VR device 104 may also incorporate respiratory measurements, such as those obtained by a microphone 142 of the VR device 104, or a skin temperature/moisture obtained by respective sensors (e.g., temperature sensor 144) of the VR device 104.

Figure 4:
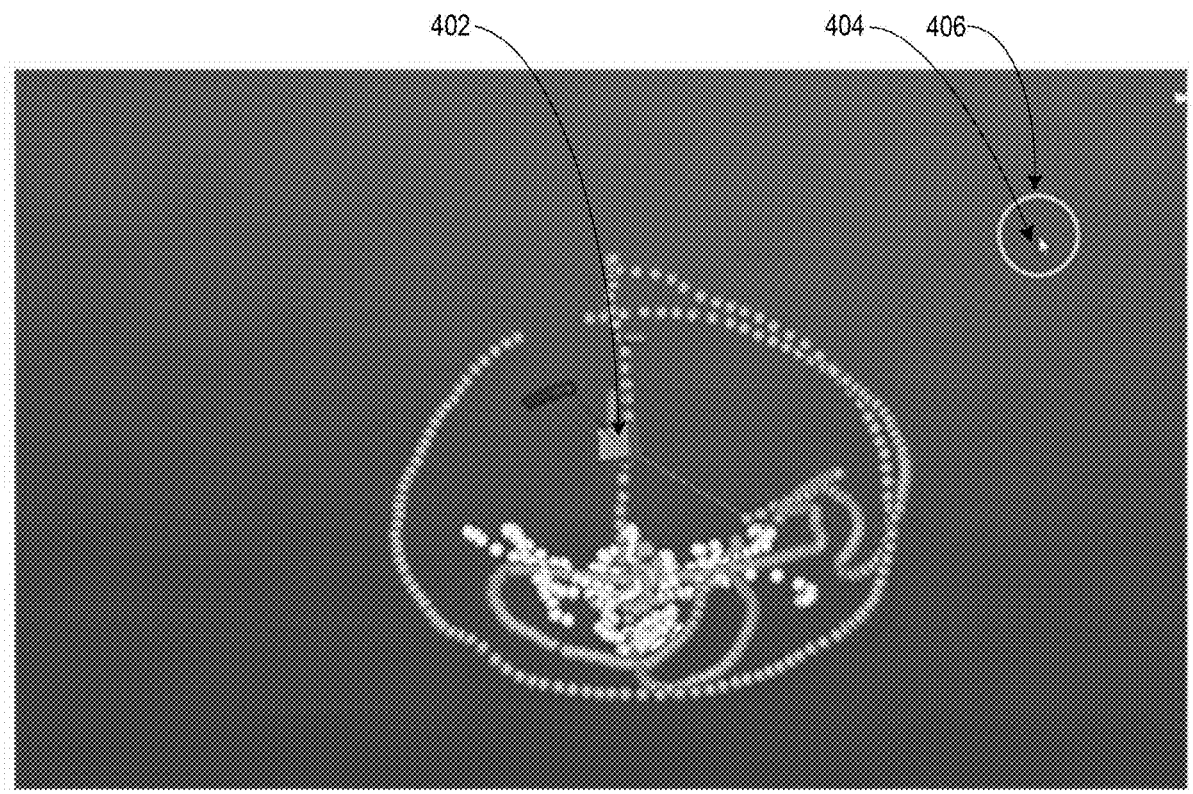
Figure 5:
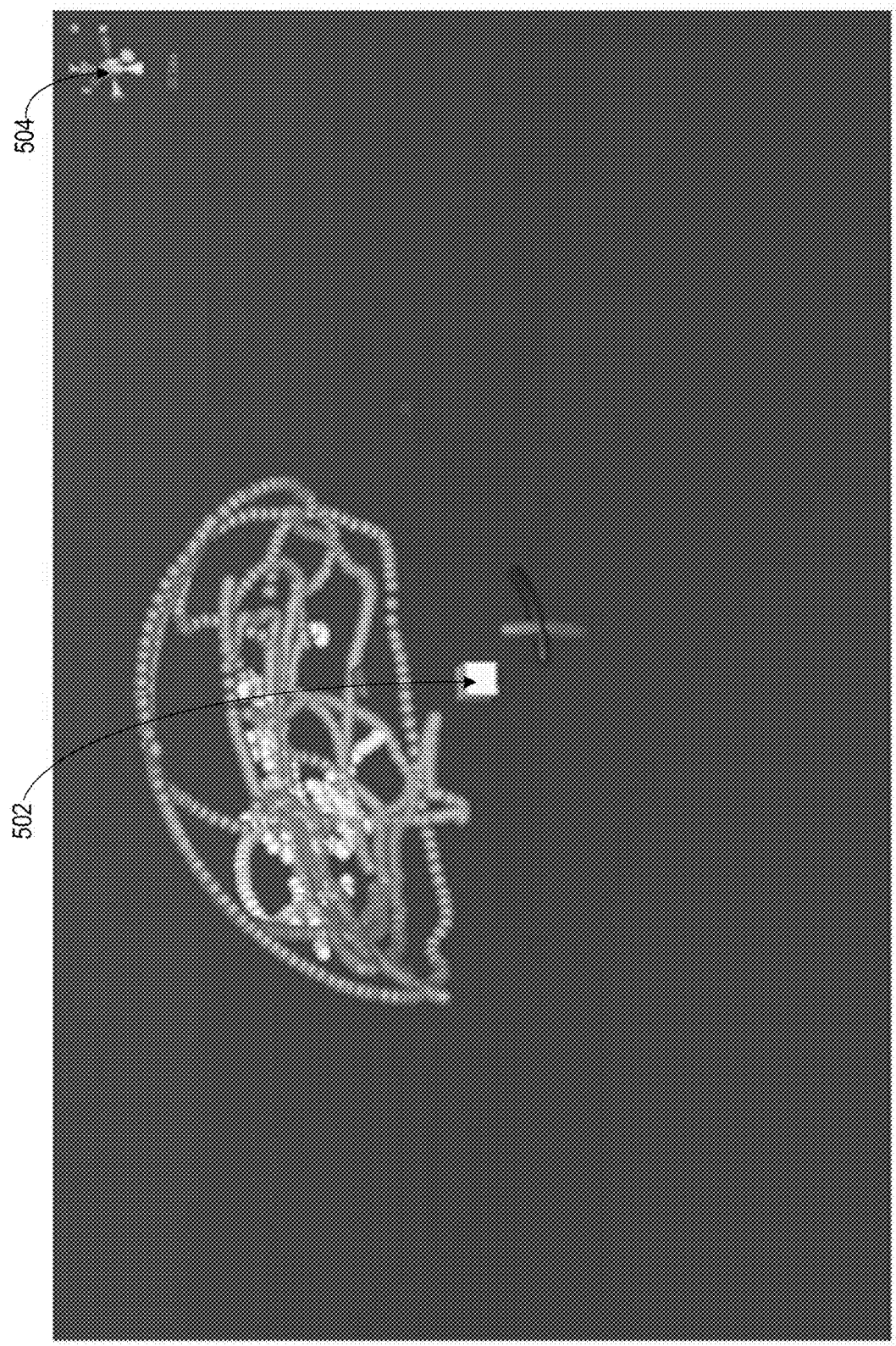

FIG. 4 depicts another example of a view direction, a head position 402, and a reference frame that can be determined for use in measuring the head movement data according to aspects of the present disclosure. The velocity and acceleration of the head movement may also be measured in some examples. The particular example of FIG. 4 also depicts a cursor element 404 and an identifier ring 406 that indicates to the provider the location of the provider cursor during analysis of the data from the VR device 104. FIG. 5 depicts still another example of a view direction, a head position 502, and a reference frame that can be determined for use in measuring the head movement data according to aspects of the present disclosure. The particular example of FIG. 5 also depicts a reference frame indicator 504.

Figure 6:
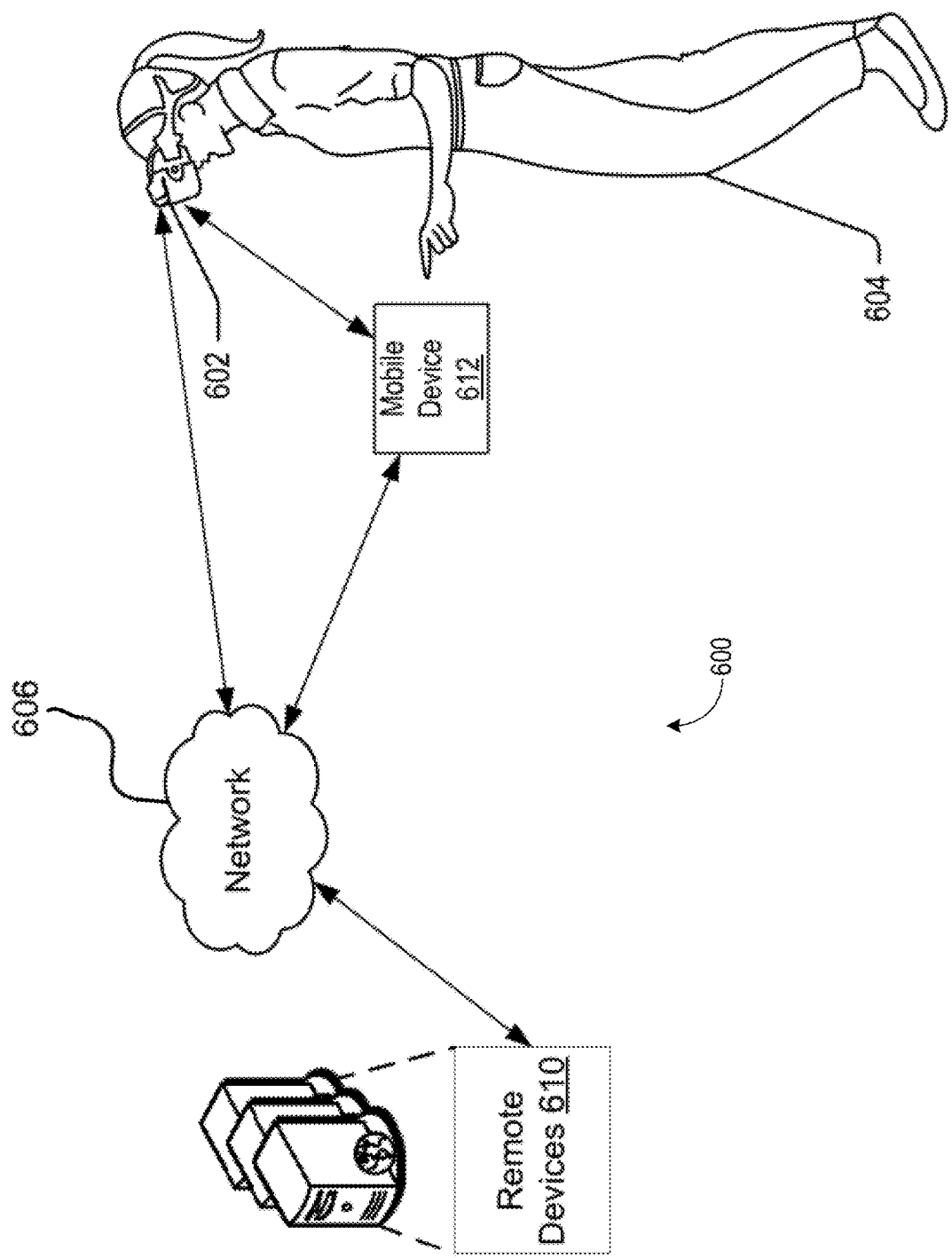
FIG. 6 is a block diagram of an example of a virtual-reality computing environment for an individualized medical health treatment system according to some aspects of the present disclosure.

FIG. 6 is a block diagram of an example of a virtual-reality computing environment 600 for an individualized medical health treatment system according to some aspects of the present disclosure. For example, a VR headset 602 may be worn by a user 604. The VR headset 602 may be the same as, or different from, the VR device 104 of FIG. 1.

The VR headset 602 may communicate with a mobile device 612, the remote devices 610, or both of these. The remote device 610 may be or may include the remote device 102 of FIG. 1, in some examples. The VR headset 602 may communicate with the mobile device 612 directly using a wireless protocol such as Bluetooth, NFC, or indirectly using network 606. The VR headset 602 can also communicate with remote devices 610 by network 606. In some cases, the communication between VR headset 602 and remote devices 610 may be accomplished by hardware, software, or a combination of both.

The VR headset 602 can be coupled to sensors, such as an accelerometer 140, a GPS, a microphone 142, temperature sensor 144, or other sensors. The sensors can be internal to the VR headset 602 or external to the VR headset 602. The sensors can measure physiological characteristics of the user and transmit the physiological characteristics to the remote devices 610.

In some examples, the virtual-reality computing environment 600 can perform some or all of the operations described above. For example, the VR headset 602 can execute operations to measure various forces acting on the head of the user and to determine physiological measurements, as described with regards to FIGS. 1-5. The remote devices 610 can then make adjustments to a virtual reality environment experienced by the user based on the determined physiological measurements. For example, the remote devices 610 can transmit one or more commands to the VR headset 602 for adjusting one or more parameters 126 of the virtual reality environment generated by the VR headset 602. The commands may be input by an operator of the remote devices 610 or automatically generated by the remote devices 610, based on the physiological measurements detected by the sensors.

While the present subject matter has been described in detail with respect to specific aspects thereof, it will be appreciated that those skilled in the art, upon attaining an understanding of the foregoing, may readily produce alterations to, variations of, and equivalents to, such aspects. Any aspects or examples may be combined with any other aspects or examples. Accordingly, it should be understood that the present disclosure has been presented for purposes of example rather than limitation, and does not preclude inclusion of such modifications, variations, or additions to the present subject matter as would be readily apparent to one of ordinary skill in the art.

The invention claimed is:

1. A virtual reality (VR) device comprising:
an accelerometer;
a processor; and
a memory including instructions that are executable by the processor for causing the processor to perform operations including:
receiving data detected by the accelerometer, the data including head position data and head movement data;
determining a view direction of a user of the VR device using the head position data;
determining a heart rate of the user by using the view direction of the user to process the head movement data;
outputting the heart rate of the user to a remote device;
receiving, from the remote device, a command to adjust a VR session presented by the VR device to the user; and
adjusting, based on the command, one or more parameters of the VR session presented by the VR device.

2. The VR device of claim 1, wherein the memory further includes instructions that are executable by the processor for causing the processor to determine the heart rate of the user by performing a Fourier transform on the head movement data.

3. The VR device of claim 1, wherein the VR session corresponds to a mental health treatment.

4. The VR device of claim 1, wherein the memory further includes instructions that are executable by the processor for causing the processor to receive physiological measurements from a plurality of sensors and transmit the physiological measurements to the remote device for use by the remote device or an operator of the remote device in determining the command.

5. The VR device of claim 4, wherein the remote device is configured to automatically determine the command based on the heart rate.

6. The VR device of claim 1, wherein the remote device is configured to:
receive one or more physiological measurements from the VR device;
provide the one or more physiological measurements as input to a trained machine learning component to receive an output from the machine learning component; and determine the command based on the output from the machine learning component.

7. The VR device of claim 1, wherein the VR device is a headset configured to be worn on a head of the user.

8. A method comprising:
receiving, by a processor, data detected by an accelerometer of a virtual reality (VR) device, the data including head position data and head movement data;
determining, by the processor, a view direction of a user of the VR device using the head position data;
determining, by the processor, a heart rate of the user by using the view direction of the user to process the head movement data;
outputting, by the processor, the heart rate of the user to a remote device;
receiving, by the processor and from the remote device, a command to adjust a VR session presented by the VR device to the user; and
adjusting, by the processor and based on the command, one or more parameters of the VR session presented by the VR device.

9. The method of claim 8, further comprising determining the heart rate of the user by performing a Fourier transform on the head movement data.

10. The method of claim 8, wherein the VR session corresponds to a medical treatment.

11. The method of claim 8, further comprising transmitting physiological measurements to the remote device for use by the remote device or an operator of the remote device in determining the command.

12. The method of claim 8, wherein the remote device is configured to automatically determine the command based on a correlation in a lookup table between (i) the heart rate and (ii) the command or a therapy module associated with the command.

13. The method of claim 8, wherein the remote device is configured to:
receive one or more physiological measurements from the VR device;
provide the one or more physiological measurements as input to a trained machine learning component to receive an output from the machine learning component; and
determine the command based on the output from the machine learning component.

14. The method of claim 8, wherein the VR device is a headset configured to be worn on a head of the user.

15. A non-transitory computer-readable medium comprising program code that is executable by a processor for causing the processor to perform operations comprising:
receiving a heart rate determined by a virtual reality (VR) device from data detected by an accelerometer of the VR device, the data including head position data and head movement data, the heart rate being of a user wearing the VR device during a VR therapy session;
comparing the heart rate to a threshold heart rate;
in response to comparing the heart rate to the threshold heart rate, determining a modification to the VR therapy session;
generating a command for controlling one or more parameters of the VR therapy session presented by the VR device in accordance with the modification; and
transmitting the command to the VR device.

16. The non-transitory computer-readable medium of claim 15, further comprising program code that is executable by the processor to:
receive one or more physiological measurements from the VR device;
provide the one or more physiological measurements as input to a trained machine learning component to receive an output from the machine learning component; and
determine the command based on the output from the machine learning component.

17. The non-transitory computer-readable medium of claim 15, further comprising program code that is executable by the processor to:
receive, from the VR device, a plurality of physiological measurements generated by a plurality of different types of sensors in relation to the user; and
determine the command based on the plurality of physiological measurements.

18. The non-transitory computer-readable medium of claim 15, further comprising program code that is executable by the processor to:
receive one or more physiological measurements from the VR device; and
determine the command based one a correlation in a lookup table between (i) the one or more physiological measurements and (ii) the command or a therapy module associated with the command.

19. The non-transitory computer-readable medium of claim 15, further comprising program code that is executable by the processor to:
receive one or more physiological measurements from the VR device; and
determine the command by applying an algorithm to the one or more physiological measurements.

20. The non-transitory computer-readable medium of claim 15, wherein the modification involves transitioning from a first audio output to a second audio output in the VR therapy session.

* * * * *